United States Patent [19]
Dennehey et al.

[11] Patent Number: 5,224,921
[45] Date of Patent: Jul. 6, 1993

[54] SMALL VOLUME COLLECTION CHAMBER

[75] Inventors: T. Michael Dennehey, Arlington Heights; Joseph C. West, Jr., Lake Villa, both of Ill.

[73] Assignee: Baxter International Inc., Deerfield, Ill.

[21] Appl. No.: 531,175

[22] Filed: May 31, 1990

[51] Int. Cl.$^5$ ............................................. B04B 5/02
[52] U.S. Cl. .................................. 494/18; 494/21; 494/37; 494/45
[58] Field of Search ............... 494/18, 45, 17, 21, 494/37; 128/DIG. 24; 604/403, 408, 410

[56] References Cited

U.S. PATENT DOCUMENTS

| | | | |
|---|---|---|---|
| 4,098,456 | 7/1978 | Bayham | 494/17 |
| 4,146,172 | 5/1979 | Cullis et al. | 494/17 |
| 4,316,576 | 2/1982 | Cullis et al. | 494/37 |
| 4,734,089 | 3/1988 | Cullis | 494/27 |
| 4,830,510 | 5/1989 | Bellhouse | 366/219 |
| 4,940,543 | 7/1990 | Brown et al. | 494/18 |

Primary Examiner—Harvey C. Hornsby
Assistant Examiner—Reginald L. Alexander
Attorney, Agent, or Firm—Paul C. Flattery; Bradford R. L. Price; Robert M. Barrett

[57] ABSTRACT

A device and method are provided for separating mononuclear cells from red blood cell depleted plasma in a centrifuge blood cell separator. The device includes an inlet for receiving plasma, an area for receiving mononuclear cells, and an outlet for receiving mononuclear cell depleted plasma. The distance and flow path between the inlet and outlet being so constructed and arranged as to cause mononuclear cells to sediment out into the area for receiving the mononuclear cells and causing at least 66% of the platelets contained in the plasma to flow to and through the outlet.

31 Claims, 2 Drawing Sheets

SMALL VOLUME COLLECTION CHAMBER

BACKGROUND OF THE INVENTION

The present invention is generally directed to the centrifugal treatment of liquids. More specifically, the present invention is directed to the separation of components from blood or plasma.

Whole blood can be separated or fractionated into its various individual components by utilizing a centrifugal blood separator. In an intervivos blood processing apparatus, whole blood can be taken from a live donor, passed through the apparatus, and then returned to the donor. During the passage of the blood through the apparatus, the blood can be separated or fractionated into its component parts, e.g., plasma, red blood cells, platelets, and other components. Some portion of these fractions can be selectively retained within a suitable storage member and other portions of the fractions can be returned to the donor.

Various types of apparatus are utilized for the intervivos processing of blood. One type of apparatus is described in U.S. Pat. Nos. 3,489,145 and 3,655,123. The apparatus utilizes a centrifugal separator element in the form of a rotatable driven bowl-shaped outer shell within which a cylindrically-shaped center or filter piece is suspended to form a narrow sleeve-shaped separation chamber of very precise dimensions. Fluid connections are established within the chamber by use of a rotating seal, the chamber having an axially-aligned inlet port at one end for admitting whole blood, and a trio of collection ports at the other end for removing red blood cells, white blood cells, and plasma components separated during centrifugation.

Systems for carrying out intervivos blood processing typically include a separation chamber within which whole blood from a donor is subjected to a centrifugal force field. Because of the differences in density, the blood components are congregated in zones at different radial distances from the center rotation of the separation chamber. Collection ports in the chamber remove the components from these zones for storage or recirculation.

In separating the components, it is necessary for the separated components to be consistently of high purity. If the blood components are subjected to intermixing, it is necessary to discard at least a portion of the separated components providing an effective lower yield for the system.

U.S. Pat. No. 4,146,172 discloses, in an embodiment, an intervivos blood processing system including processing chambers for centrifugally separating red blood cells, and platelet components from whole blood. An example of such a system is the CS-3000® sold by Baxter Healthcare Corp., Deerfield, Ill.

The system includes a thin processing chamber having first and second closely spaced side walls defining an interior chamber including at least one collection region, outlet means for withdrawing fluid from the collection region of the chamber, and means including inlet means and an additional outlet means defining a flow path for delivering blood to be processed to the chamber. Means including a rotatably driven carriage are provided for rotating the chamber with the chamber mounted generally perpendicular to a radius of the rotor whereby the red blood cell component is caused to collect in the collection region of the chamber.

Although the described system functions satisfactorily for separating red blood cells and platelets from whole blood, for certain applications such as, separating mononuclear cells, this system may not function optimally. When so used, the collection chamber tends to retain platelets leading to a mononuclear cell product that is contaminated with platelets. Typically, at least approximately 50% of the platelets are retained within the collection chamber. It has been found that a retention of over one-third of the platelets in the mononuclear cell product does not provide a satisfactory product for certain applications.

The retention of platelets within the collection chamber not only represents a disadvantage because mononuclear cells and the platelets are intermixed but also can have deleterious effects on the donor. Donor thrombocytopenia is associated with multiple frequent donations of mononuclear cells due to a loss of platelets.

Known collection chambers typically are also too large for a mononuclear cell collection process. For example, one commercially utilized chamber has a volume of approximately 200 cc. This is generally considered too large for the collection of mononuclear cells, i.e., for a stem cell procedure. With such a large volume chamber, additional volume reduction is required and/or additional processing such as a density separation using Ficol-Hypaque to remove the platelets is necessary.

SUMMARY OF THE INVENTION

The present invention provides a means for the efficient collection of mononuclear cells. In an embodiment, a collection chamber is provided to be utilized with a centrifugal blood cell separator for collecting mononuclear cells. The performance characteristics of the chamber make it highly desirable for use in collecting stem cells to be used for bone marrow transplants. A method of collecting mononuclear cells is also disclosed.

In an embodiment, a device for separating mononuclear cells from red blood cell depleted plasma for use in a centrifugal blood separator is provided. The device includes an inlet for receiving the plasma, an area for receiving mononuclear cells, and an outlet for receiving mononuclear cell depleted plasma. The distance and flow path between the inlet and outlet is so constructed and arranged that it causes mononuclear cells to sediment out into the area for receiving the mononuclear cells and causes at least two-thirds of the platelets contained in the plasma that is received by the device to flow through the outlet and not be retained within the area for receiving mononuclear cells.

In an embodiment, the device includes a container having the inlet, outlet, and area for receiving mononuclear cells.

In an embodiment of the present invention, the centrifugal blood separator exerts at least four different G forces on the device: the inlet experiencing a G force of R3; the outlet a G force of R2; the cavity a G force of R5; and a path between the inlet and outlet a G force of R1, wherein R5>R3>R2>R1.

In a further embodiment of the present invention, a container for receiving mononuclear cells separated from red blood cell depleted plasma, for use in a blood separator, is provided comprising an inlet for receiving the plasma and defining an inlet flow path, an outlet for receiving mononuclear cell depleted plasma and directing the mononuclear cell plasma out of the container, the outlet defining an outlet flow path, and a cavity for receiving mononuclear cells. Means are provided for causing at least two-thirds of the platelet cells contained in the plasma to be directed from the inlet flow path to the outlet flow path and out of the container and for causing mononuclear cells to sediment out into the cavity.

In an embodiment, the inlet includes a substantially straight portion that terminates into a dogleg portion.

In an embodiment, the inlet has a sufficiently small cross-sectional shape to ensure the velocity of the plasma in the inlet flow path is sufficiently great.

In an embodiment, a chamber for separating mononuclear cells from a red blood cell depleted plasma in a centrifuge blood processing system is provided. The chamber comprising a flexible container including a cavity for receiving mononuclear cells and including an inlet and an outlet. A first plate is provided including recessed means for defining within the container an inlet path, the cavity, and an outlet path. The chamber includes a second plate that mates with the first plate for sandwiching the container therebetween. The inlet path and outlet path define means for causing mononuclear cells to sediment out into the cavity and for causing at least two-thirds of the platelets in the plasma that enter the container through the inlet to exit the container through the outlet.

In an embodiment, the inlet path includes a first substantially straight portion that terminates in a dogleg portion that terminates in a second substantially straight portion substantially perpendicular to the first substantially straight portion.

In an embodiment, the outlet path includes a substantially straight portion.

In an embodiment, at least 80% of the platelets in the plasma do not sediment out into the cavity.

In an embodiment of the invention, a method for separating mononuclear cells from a red blood cell depleted plasma is provided. The method comprising the steps of exerting a centrifugal force on the plasma and causing the plasma to flow in a first inlet fluid path. The plasma is then caused to flow in a second fluid path above an area for receiving mononuclear cells, at a sufficient speed and over a sufficiently short distance to cause at least two-thirds of the platelets in the plasma to flow out of the container, but causing mononuclear cells to sediment out into the cavity. The plasma is then caused to flow in a third outlet flow path.

In an embodiment of the method, the G forces on the plasma during the centrifugal process are as follows:

R3 on at least a first portion of the first flow path;
R1 at the second flow path; and
R2 at the third flow path; wherein:
R3>R2>R1.

In a further embodiment, the G forces at the cavity are R5 and R5>R3>R2>R1. In a further embodiment, the G forces at a second portion of the first flow path are R4 and R5>R4>R3>R2>R1.

In an embodiment, the plasma is removed intervivos from a patient/donor and the plasma after exiting the third outlet flow path is reinfused into the patient/donor.

Additional features and advantages of the present invention are described in, and will be apparent from, the detailed description of the presently preferred embodiments and from the drawings.

DETAILED DESCRIPTION OF THE PRESENTLY PREFERRED EMBODIMENTS

The present invention is directed to a means for efficiently collecting mononuclear cells. In an embodiment, a collection chamber for use in a centrifugal blood cell separator for collecting mononuclear cells is provided, as well as a method of collecting mononuclear cells.

In the illustrated embodiment of the present invention, the mononuclear cell separation chamber of the present invention is designed to be utilized with a centrifugal blood separator such as that disclosed in U.S. Pat. No. 4,146,172, the disclosure of which is incorporated herein by reference. However, it should be appreciated, that the present invention can be used with other centrifuge blood cell separators and devices to collect mononuclear cells.

The illustrated embodiment of the mononuclear cell separation chamber of the present invention functions to separate mononuclear cells from red blood cell depleted plasma. The performance characteristics of the mononuclear cell separation chamber of the present invention make it highly desirable for collecting stem cells to be used for bone marrow transplants. In the illustrated embodiment of the mononuclear cell separator chamber, the chamber functions as a secondary or collection chamber in a centrifuge blood cell separator such as, for example, the CS-3000® sold by Baxter Healthcare Corp. In such a blood cell separator, a primary or separation chamber is provided that separates the red blood cells from the whole blood. The red cell depleted plasma, which preferably also includes an anticoagulant solution, comprises a platelet rich plasma component that flows from the primary or separation chamber to the secondary or collection chamber. The red cell depleted plasma includes mononuclear cells.

Figure 1:
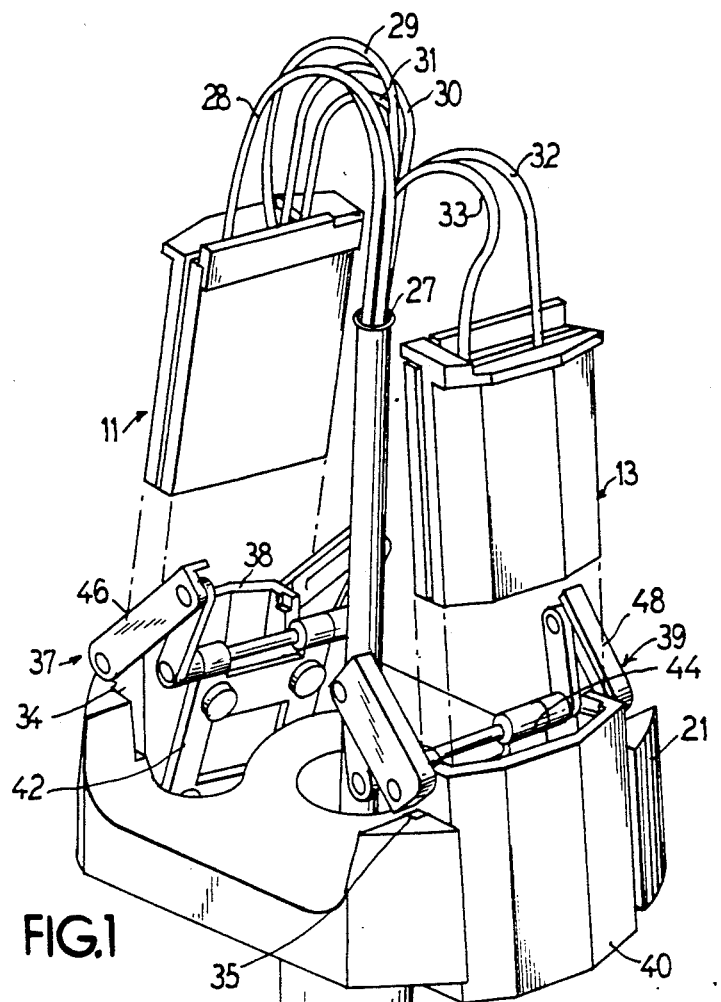
FIG. 1 illustrates a perspective view of a rotor portion of the centrifuge blood processing apparatus illustrating processing chambers prior to insertion into the rotor.

By way of example, reference is made to U.S. Pat. No. 4,146,172 (which is incorporated herein by reference) that describes a blood processing system in which the invention can be utilized. The blood processing system includes a rotor which is illustrated in FIG. 1 and will now be discussed in more detail with reference to an embodiment of the instant invention.

The blood processing system includes a centrifugation apparatus having a rotor drive assembly to which a rotor assembly or carriage 21 is journaled by means of a hollow support shaft 23. The rotor drive assembly (not shown) is itself journaled to a stationary hub assembly by means of a vertical drive shaft. A guide sleeve 25 is mounted on the rotor drive assembly.

A red blood cell separation chamber and a mononuclear cell separation chamber 13 are removably received by the rotor assembly 21. The rotor assembly 21 functions to impart centrifugal forces onto the chambers 11 and 13 and the fluids fed therethrough. Fluid communication is established between the two chambers 11 and 13, which rotate with the rotor assembly 21, and the processing system, by means of an umbilical cable 27, that includes numerous tubes 28, 29, 30, 31, 32, and 33 that define fluid channels. The umbilical cable 27 extends from a central location along the axis of rotation of the rotor downwardly through the center of the drive shaft 23, radially outwardly through guide sleeve 25. As discussed in detail in U.S. Pat. No. 4,146,172, whole red blood is taken from a donor/patient and fed to the chambers 11 and 13 via the umbilical cable 27.

The routing of the umbilical cable 27, together with the rotor assembly 21 and rotor assembly are driven in the same direction and establishes fluid communication between chambers 11 and 13 without the cable becoming twisted. Instead, the umbilical cable 27 is subjected only to flexing, or repeated partial twists about its axis through angles not in excess of 180 degrees, as the rotor assembly 21 rotates. The rotor and rotor drive assembly are described in detail in U.S. Pat. No. 4,146,172.

As illustrated in FIG. 1, the rotor carriage 21 includes two slotted areas 34 and 35 for removably receiving clamps 37 and 39, respectively. The clamps 37 and 39 are designed to removably secure the chambers 11 and 13, respectively, within the carriage 21. To this end, the clamps 37 and 39 include a first surface 38, 40 and second surface 42, 44. Arm members 46 and 48 are provided for pivoting the second surface 42, 44 toward the first surface 38, 40. The arm members 46 and 48 function to open and close the clamps 37 and 39. When closed, the clamps 37 and 39 secure the chambers 11 and 13 therebetween allowing the rotor assembly to impart a centrifugal force to the chambers.

It is desirable that the carriage 21 and/or clamps 37 and 39, as well as a portion of the chambers 11 and 13 be formed of a material of high thermal conductivity, such as aluminum, so that the temperature of the blood passing through the chambers can be more readily controlled. A resistance heating element or other active thermal element such as a hot air blower, can be provided in thermal communication with the rotor to heat the carriage 21 and clamps 37 and 39 to a desired temperature, typically body temperature or 37° C., during processing. This provides for more consistent and efficient sedimentation, and reduces the possibility of thermal shock as the processed blood is reintroduced into the donor.

Under the influence of a centrifugal force field imparted by the rotor, whole blood within the separation chamber 11 is caused to separate, with the heavier red blood cells collecting at collection regions within the chamber. The less dense platelet rich plasma component remains primarily outside of the collection regions. In the preferred embodiment, the platelet rich plasma component will include what is commonly referred to as the buffy coat portion of blood, that includes white cells and also the mononuclear cells that are targeted for collection with the device and method of the present invention.

The separated red blood cell component is removed from chamber 11 through at least one of the tubes along the top margin thereof which communicates with the collection regions of the chamber. The collection port or tube is connected to a further tubing segment allowing the red blood cells to be further processed, collected, or the like. One of the tubing members removes the resultant platelet rich plasma (or red blood cell depleted plasma) component from the separation chamber 11. The red blood cell depleted plasma is then fed into the mononuclear cell separation chamber 13 through tube 33 wherein the mononuclear cells can be separated. As set forth in U.S. Pat. No. 4,146,172, the red blood cell depleted plasma can be fed from the separation chamber 11 to the chamber 13 using a variable-rate pump assembly (not shown).

In the mononuclear cell separation chamber 13 of the present invention, mononuclear cells are removed, as set forth in more detail below, leaving a solution of mononuclear cell poor plasma that is conveyed through a tubing segment 32 for further separation or to be reinfused into the donor. Due to the present invention, the resultant mononuclear cell depleted plasma includes at least a substantial majority of the original platelets present therein.

Figure 2:
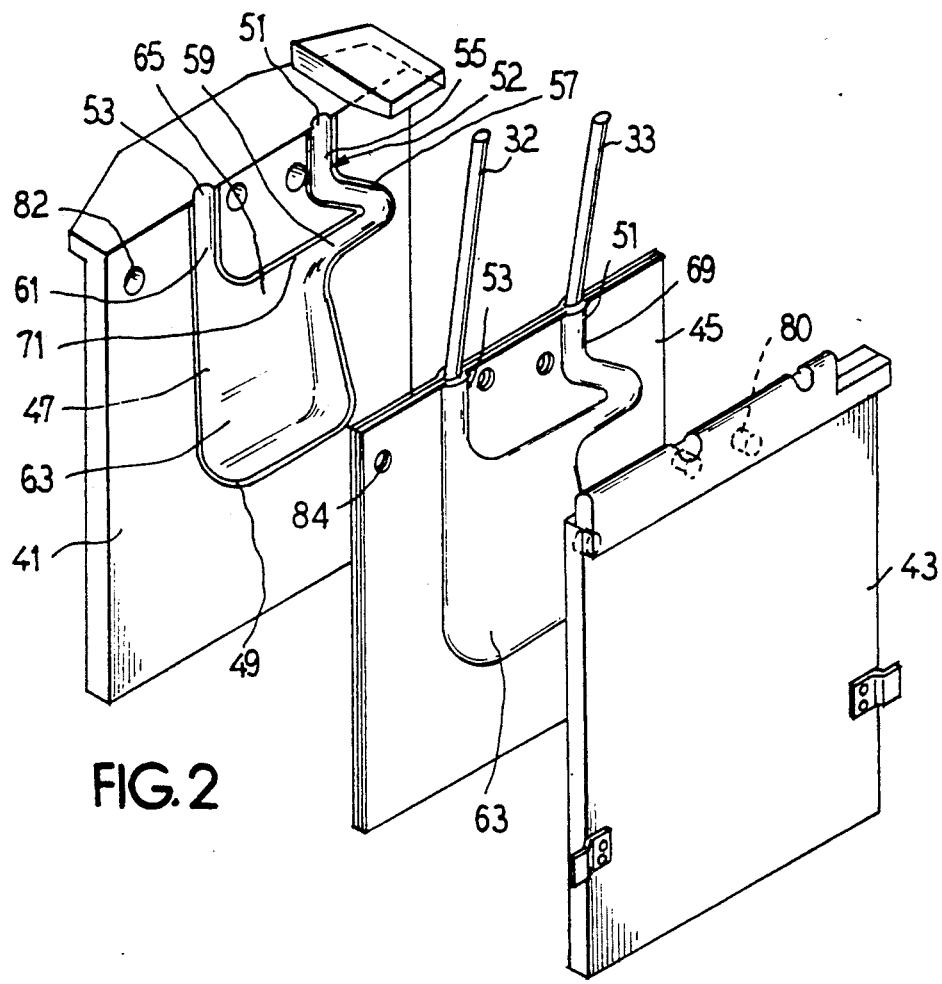
FIG. 2 illustrates an exploded perspective view of an embodiment of the mononuclear cell separation chamber of the present invention.

Referring now to FIG. 2, an embodiment of the mononuclear cell separation chamber 13 of the present invention is illustrated. As illustrated, the chamber 13 comprises a first plate or platen 41 and a second plate or platen 43 that sandwich therebetween a flexible container 45. The plates 41 and 43, between which the container 45 is sandwiched, as illustrated in FIG. 1, are slidably received within the clamp 39 that is slidably received in a slot 35 on the carriage 21 of the rotor assembly.

The mononuclear cell separation chamber 13 is specifically constructed so as to cause the mononuclear cells to be retained within the flexible container 45 during the centrifuge separation process. As set forth in detail below, under the influence of a centrifugal force, the red blood cell depleted plasma within the flexible bag 45 is caused to separate, mononuclear cells sediment out into the flexible container and the remaining plasma including at least two-thirds, and preferably 80%, of the platelets exiting the bag at an exit port.

The first plate 41 is constructed from a semi-rigid plastic material such as, for example, polyurethane. The semi-rigid plastic material is flexible enough to seal the container 45 around a periphery of a cavity or recess 47 to produce a specific container/cavity shape, yet is sufficiently rigid to maintain the cavity shape while under centrifugation forces of 340 to 390 g or more. The first plate 41 may of course also be made of a rigid material such a aluminum for greater resistance to Deformation under high g forces.

To ensure that a shape is imparted to the container 45 by the first plate 41, the first plate includes a bead portion 49. The bead 49 seals the flexible container 45 when the container is sandwiched between the plates 41 and 43. The recessed region 47 of the plate 41 thereby defines the container's 45 shape and therefore defines the flow path when the container is sandwiched between the plates 41 and 43.

As illustrated in FIG. 2, the recess region 47 of the plate 41 and the bag 45 includes an inlet 51 and an outlet 53. The inlet 51 defines an inlet fluid path 52. The inlet fluid path 52 includes a first substantially straight fluid path 55 that extends to a dogleg fluid path 57. The inlet path 52 terminates as a second substantially straight fluid path 59 that is substantially perpendicular to the first substantially straight fluid path 55. The inlet fluid path 52 defines a fluid flow path for the red blood cell depleted plasma entering the chamber 13.

An outlet fluid path 61 is provided on an opposite side of the container 45 and plate 41. The outlet fluid path 61 is substantially straight and is substantially parallel to the first substantially straight fluid path 55 of the inlet fluid path 52. The outlet fluid path 61 defines a fluid path from an interior of the container 45 to the tube 32.

Figure 3:
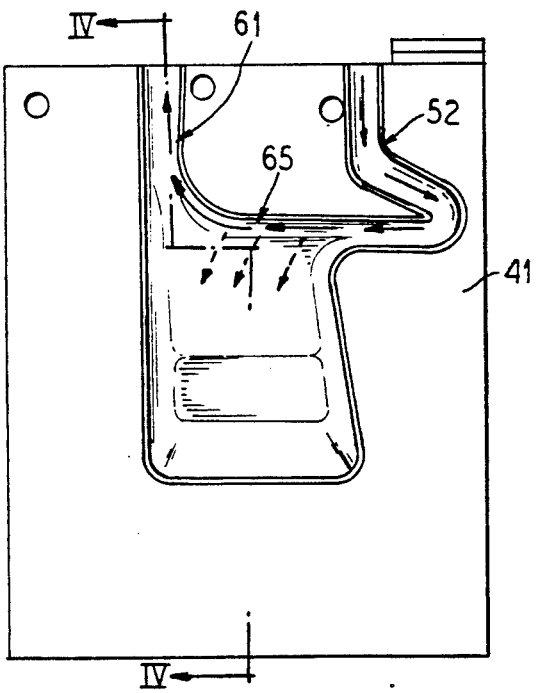
FIG. 3 illustrates a perspective view of an embodiment of a plate of the mononuclear cell separation chamber of the present invention illustrating the fluid flow path.

A cavity 63 for collecting mononuclear cells is located between the inlet 51 and outlet 53. Referring now to FIG. 3, the flow path of plasma within the container 45 is illustrated. As illustrated, the red blood cell depleted plasma flows from the inlet 51 into the container 45. A short fluid flow path 65 is provided between the inlet fluid flow path 52 and the outlet fluid flow path 61. Due to this short arcuate fluid flow path 65 defined by the chamber 13, at least a substantial majority of the platelet rich plasma is caused to flow from the inlet 51 toward the outlet 52 and out through the container 45 sandwiched between the plates 41 and 43. However, due to the chamber's 13 structure, as well as the cell density and sedimentation characteristics of the mononuclear cells, the mononuclear cells are caused to sediment out and flow into the cavity 63 of the container 45, this is indicated in the figures as broken arrows. In order to assist in purging air during priming, the top of fluid path 59, 65 should be angled slightly upwardly in the direction toward the outlet flow path 61.

The second plate 43 includes a substantially flat surface that mates with the first plate 41. The second plate 43 is designed so that the substantially flat surface mates with the first plate 41 trapping the container 45 therebetween and accommodating the inlet and outlet tubings 33 and 32. To this end, the second plate 43 can include projections 80 that are received by apertures 82 in the first plate 41. To secure the flexible container 45 in place, in the illustrated embodiment, the flexible container 45 also includes apertures 84. Preferably, the second plate 43 is constructed from aluminum to provide, as previously discussed, heat transfer characteristics.

Figure 5:
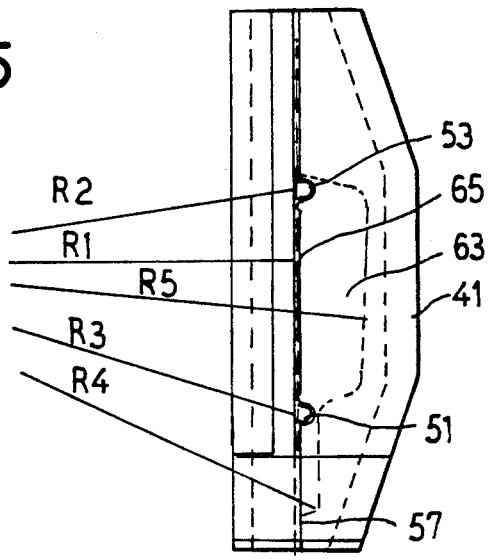
FIG. 5 illustrates a perspective view of the plate of FIG. 3 illustrating the associated G forces thereon.

FIG. 5 illustrates the relative G forces that act upon the chamber 13 during the centrifuge process: R1 representing the lowest G force and R5 the highest G force. At least five principal G forces R1, R2, R3, R4, and R5 (R5>R4>R3>R2>R1) are exerted on the container 45 during the centrifuge process. The G forces influence the flow of the plasma within the container 45. The flow path and associated G forces within the container 45 during the centrifuge process are as follows.

A red blood cell depleted plasma enters through the inlet 51 through tubing 33. The plasma, in the illustrated embodiment, has been depleted of red blood cells by being fed through the primary or separation chamber 11. Initially, upon entering the inlet 51 and specifically the first substantially straight fluid path 55 of the inlet fluid path 52, the plasma is subjected to a midrange G force of R3. The plasma is then routed along the inlet fluid path 52 to the dogleg fluid path 57 wherein a G force of R4 is exerted. Accordingly, at the dogleg fluid path 57 a somewhat greater G force is exerted on the plasma then initially exerted at the first substantially straight portion 55 of the inlet fluid path 57. The dogleg portion 57 of the inlet fluid path 52 orients the fluid flow path and begins the sedimentation process of the mononuclear cells. In order to insure that the solution velocity is sufficiently high, the walls 69 define an inlet fluid path 52 having a sufficiently small cross-sectional shape.

The plasma flows from the dogleg portion 57 of the inlet fluid path 52 to a second substantially straight fluid path 59 toward the outlet fluid path 61. The red blood cell depleted plasma, flows across the top 71 of the cavity 63 toward the outlet 53. Due to the short flow path 65 across the top 71 of the container 45 between the inlet 51 and outlet 53, the effective surface area for the low density platelet minimizes the platelet collection potential of the container 45.

The higher density mononuclear cells, that have begun to sediment within the dogleg fluid flow portion 57 of the inlet flow path 52, flow smoothly into the cavity 63 wherein the highest G force, R5, is exerted. The cavity 63 functions as a reservoir for collecting mononuclear cells due to its large volume, flow rate, radiussed inlet and outlet port, and low turbulence characteristics.

The lowest G field R1 is at the top 71, center of the container 45 across which the platelet rich plasma flows. The outlet port 53 has a slightly higher G field, R2, exerted thereon then at the top center 71 of the container 45. Therefore, the outlet fluid path 61 functions to remove the plasma and the platelets that are still suspended but have started to sediment. As previously stated, the back surface of the cavity 63 presents the highest G field R5 and is radiussed to present an even G field from side to side of the chamber allowing the mononuclear cells to sediment out into the cavity 63.

Figure 4:
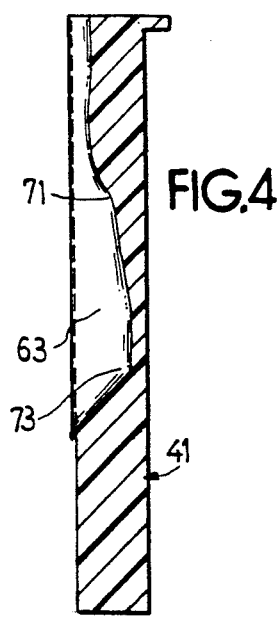
FIG. 4 is a cross-sectional view of the plate of FIG. 3 taken along lines IV—IV of FIG. 3.

As illustrated in FIG. 4 the cavity 63 is slanted inward from bottom 73 to top 71 to present the maximum G field R5 at the bottom. The mononuclear cells tend to slide to the maximum G area and then accumulate until the cavity 63 is filled and is disturbed by the plasma flow. When the cavity 63 has been filled with the mononuclear cells, the container 45, and specifically the cavity 63, ceases to collect mononuclear cells and all cells pass through the container 45 to be returned to the patient/donor.

In an embodiment, preferably, the overall volume of the container 45 is approximately 50 cc. The effective mononuclear cell trapping volume of the cavity 63 is approximately 35 cc. The chamber 63 of the present invention has been found to recover mononuclear cells while retaining only approximately 5 to about 20% of the platelets contained within the platelet rich plasma from which the mononuclear cells are removed.

The container 45 can be constructed from a variety of materials. For example, the container 45 can be constructed from polyvinylchloride or other hemocompatible plastic that is sealed along at least three edges to define a container.

It should be noted that although it is not necessary that the chamber 13 serve as the secondary chamber in a device such as that disclosed in U.S. Pat. No. 4,146,172, in order to obtain optimal recovery of mononuclear cells, the plasma should be somewhat depleted of red blood cells.

As previously stated, the present invention can be utilized to collect mononuclear cells including stem cells for bone marrow transplantation. The present invention can also be utilized, for example, to collect: peripheral stem cells for cell culture/research; monocytes for cell culture/research and treatment of fungal infection; and lymphocytes for cell culture/research.

It should be noted that the plates 41 and 43 and container 45 of chamber 13 are not critical to the present invention. Instead, it is the flow path that allows the present invention to capture the mononuclear cells. Accordingly, a variety of other structures can be utilized to separate out the mononuclear cells from red blood cell depleted plasma or platelet rich plasma. An example of such a device would be an integral structure wherein a container or other means imparts a flow path such as that imparted by the chamber 13 of the present invention. It is also possible to utilize in a centrifugal device a 360° flow path wherein a variety of flow paths are dictated therein. One such flow path would provide a short arcuate path from an inlet portion to an outlet portion causing the mononuclear cell components to sediment out into a reservoir.

By way of example, and not limitation, an example of the present invention and method of using same will now be given.

The chamber 13 constructed in accordance with the illustrated embodiment set forth in the figures of this application is used as a collection chamber in a CS-3000 TM Blood Cell Separator available from Baxter Healthcare Corporation, Deerfield, Ill. The mononuclear cell collection procedure used on the CS-3000 TM Blood Cell Separator (with a closed system apheresis kit) yields a high-efficiency mononuclear cell collection with minimal red blood cell contamination.

To achieve this collection, the depth into the cell layer is increased and the interval between mononuclear cell collections is decreased to approximately three-to-four minutes. Also, the whole blood volume processed is increased to the desired amount.

At the end of the collection, maximum red blood cells are returned to the donor/patient by reinfusing.

The CS-3000 TM is set to the following parameters to collect mononuclear cells.

| CS-3000 RUN PARAMETERS | |
|---|---|
| Parameters | Preset |
| Separation Chamber | GRANULO |
| Collection Chamber | Chamber 13 illustrated in Figures |
| Blood Flow Rate | 50 ml or higher |
| WB:ACD-A ratio | 10 to 11:1 |
| Centrifuge Speed | 1600 RPM |
| Interface Detector Offset | 100 to 150 |
| Endpoint Volume | 7000 ml or greater |
| Run Time | 140 minutes or more |

Thirty-nine patients/donors runs were performed pursuant to the above procedure.

The efficiency of the run is the percentage derived by dividing the number of platelets collected in the container by the number of platelets presented to the container during the run. Since an important goal when collecting mononuclear cells is to minimize the number of platelets collected with those mononuclear cells, a lower efficiency results in better performance. The results were as follows:

| Number of Runs (Donor/Patients) | 39 |
|---|---|
| Avg. Platelets in Container | 19% efficiency |
| Standard Deviation | 8% |
| Lowest Platelet Total | 5% efficiency |
| Highest Platelet Total | 34% efficiency |

It is noted that only some runs were performed on patients, while others were performed on healthy donors. Patients are more likely than healthy donors to have lower platelet, red blood cell, and/or white blood cell counts.

Accordingly, the efficiency figures may be higher, and therefore the performance may actually be lower, than would be obtained if patients only were the subjects for generating the data. With the 34% efficiency noted in the above table, by definition 66% of the platelets exit the container.

As illustrated above, the chamber 13 of the present invention functioned to capture mononuclear cells while only trapping, on average, 19% of the platelets that were present in the plasma. Indeed, the greatest number of platelets in any run was 34% which, although not optimal, is deemed acceptable.

It should be understood that various changes and modifications to the presently preferred embodiments described herein will be apparent to those skilled in the art. Such changes and modifications can be made without departing from the spirit and scope of the present invention and without diminishing its attendant advantages. It is therefore intended that such changes and modifications be covered by the appended claims.

We claim:

1. A device for separating and collecting mononuclear cells from red blood cell depleted plasma in a centrifuge blood cell separator comprising:
   a body defining an inlet for receiving plasma, an area for receiving and collecting mononuclear cells, and an outlet for receiving mononuclear cell depleted plasma, the inlet and outlet being located at a top portion of the area; and
   the body defining a flow path directly from the inlet to the outlet located at a top portion of the area, the distance and flow path between the inlet and outlet being so constructed and arranged as to cause mononuclear cells to sediment out and collect in the area for receiving and collecting the mononuclear cells and causing at least 66% of the platelets contained in the plasma to flow to and through the outlet.

2. The device of claim 1 including a container having the inlet, outlet, and area for receiving mononuclear cells.

3. The device of claim 1 including:
   an at least-semi-rigid plate including recessed areas defining an inlet, outlet, and an area for receiving mononuclear cells;
   a substantially rigid plate for mating with the at least semi-rigid plate; and
   a flexible container that is sandwiched between the substantially rigid wall and semi-rigid wall for receiving the mononuclear cells.

4. The device of claim 1 wherein the centrifuge blood cell separator exerts at least four different G forces on the device, at least a portion of an inlet fluid path experiencing a G force of R3, at least a portion of an outlet fluid path a G force of R2, at least a portion of the cavity a G force of R5, and at least a portion of a fluid path between the inlet and outlet a G force of R1, wherein:
   $R5 > R3 > R2 > R1$.

5. The device of claim 1 wherein, on average, at least 80% of the platelets flow through the outlet.

6. A container for receiving and collecting mononuclear cells separated from red blood cell depleted plasma, for use in a blood separator comprising:

a body defining a cavity for receiving and collecting mononuclear cells and including an inlet for receiving plasma and defining an inlet flow path and an outlet for receiving plasma and directing the plasma out of the cavity, the outlet defining an outlet flow path, the inlet and outlet being located at a top portion of the cavity; and the body defining a flow path directly from the inlet flow path to the outlet flow path at a top portion of the cavity, the distance between the inlet and outlet being such that at least 66% of the platelet cells contained in the plasma are caused by the inlet flow path to be directed to the outlet flow path and through the outlet and mononuclear cells sediment out and are collected in the cavity.

7. The container of claim 6 wherein the inlet flow path includes a substantially straight portion that terminates into a dogleg portion.

8. The container of claim 6 wherein the inlet flow path has a sufficiently small cross-sectional shape to ensure a sufficiently great velocity of the plasma through the inlet flow path.

9. The container of claim 6 including a first plate for receiving portions of the container and a second plate for mating with the first plate and sandwiching the container therebetween.

10. The container of claim 6 wherein the centrifuge blood cell separator exerts at least four different G forces on the container, at least a portion of the inlet fluid path experiencing a G force of R3, at least a portion of the outlet fluid path experiencing a G force of R2, at least a portion of the cavity experiencing a G force of R5, and a fluid path between the inlet and outlet experiencing a G force of R1, wherein:

R5>R3×R2>R1.

11. The container of claim 7 wherein the centrifuge blood separator exerts at least five different G forces on the container, at least a portion of the outlet fluid experience a G force of R2, at least a portion of the cavity experiencing a G force of R5, a fluid path between the inlet and outlet experiencing a G force of R1, the substantially straight portion experiences a G force of R3 and the dogleg portion experiences a G force of R4, wherein:

R5>R4>R3>R2×R1.

12. The container of claim 6 wherein, on average, at least 80% of the platelets that flow into the container flow out of the container.

13. A chamber for separating and collecting mononuclear cells from a red blood cell depleted plasma comprising:

a flexible container including a cavity having a top portion and a bottom portion for receiving mononuclear cells and including an inlet and an outlet;

a first plate including recessed means for defining within the container an inlet path, the cavity, and an outlet path, the inlet path and outlet path being located at a top portion of the cavity;

a second plate that mates with the first plate for sandwiching the container therebetween; and the inlet path and outlet path define means for creating a flow path across the top portion of the cavity directly from the inlet path and outlet path and for causing mononuclear cells to sediment out and collect in the cavity and cause at least 66% of the platelets in the plasma that enters the container through the inlet to exit the container through the outlet.

14. The chamber of claim 13 wherein the inlet path includes a first substantially straight portion that terminates in a dogleg portion that terminates in a second substantially straight portion substantially perpendicular to the first substantially straight portion.

15. The chamber of claim 13 wherein the outlet path includes a substantially straight portion.

16. The container of claim 13 wherein the inlet flow path has a sufficiently small cross-sectional shape to ensure a sufficiently great velocity of the plasma through the inlet flow path.

17. The device of claim 13 wherein the centrifuge blood cell separator exerts at least four different G forces on the device, at least a portion of the inlet path experiencing a G force of R3, the outlet path a G force of R2, the cavity a G force of R5, and a path between the inlet and outlet a G force of R1, wherein:

R5>R3>R2>R1.

18. The container of claim 17 wherein the inlet path includes a substantially straight portion and dogleg portion and the substantially straight portion experiences a G force of R3 and the dogleg portion experiences a G force of R4, wherein:

R5>R4>R3>R2>R1.

19. The chamber of claim 13 wherein the first plate is constructed from a semi-rigid material.

20. The chamber of claim 13 wherein the second plate is constructed from a rigid material.

21. The chamber of claim 13 wherein at least approximately 80% of the platelets in the plasma that enter the container exit the container.

22. A method for separating and collecting mononuclear cells from a red blood cell depleted plasma in a centrifuge blood separator including a device having an inlet, cavity, and outlet comprising the steps of:

causing the plasma to flow in a first inlet fluid path at a top portion of the device;

causing the plasma to flow from the first inlet fluid path directly to and in a second fluid path above an area for receiving and collecting mononuclear cells, at a sufficient speed and over a sufficiently short distance to prevent at least approximately 66% of the platelets in the plasma from sedimenting out, but allowing mononuclear cells to sediment out and collect in the cavity; and causing the plasma to flow from the second fluid path directly to a third outlet flow path located at a top portion of the device.

23. The method of claim 22 wherein the G forces exerted by the centrifuge on the plasma are as follows:

R3 on at least a first portion of the first flow path;

R1 at the second flow path; and

R2 at the third flow path; wherein:

R3>R2>R1.

24. The method of claim 22 wherein the G forces exerted by the centrifuge on the plasma are R5 at the cavity and R5>R3>R2>R1.

25. The method of claim 23 wherein the G forces at a second portion of the first flow path are R4 and R5>R4>R3>R2>R1.

26. The method of claim 22 wherein plasma is removed intervivos from a patient/donor.

27. A method of claim 26 wherein after flowing through the outlet flow path mononuclear cell depleted plasma is reinfused into the patient/donor.

28. The method of claim 22 wherein at least approximately 80% of the platelets in the plasma are prevented from sedimenting out.

29. A chamber for separating and collecting mononuclear cells and including an outlet located at a top portion of the container;
 a first plate including recessed means for defining within the container an inlet path, the cavity, and an outlet path;
 the inlet path includes a first substantially straight portion that terminates in a dogleg portion that terminates in a second substantially straight portion that is substantially perpendicular to the first substantially straight portion;
 a second plate that mates with the first plate for sandwiching the container therebetween; and
 the inlet path and outlet path define therebetween a direct flow path across a top of the cavity for causing mononuclear cells to sediment out and collect in the cavity.

30. The chamber of claim 29 wherein the outlet path includes a substantially straight portion.

31. The chamber of claim 29 wherein at least 66% of the platelets contained within the plasma entering the container exit the container.

* * * * *

UNITED STATES PATENT AND TRADEMARK OFFICE
CERTIFICATE OF CORRECTION

PATENT NO. : 5,224,921
DATED : July 6, 1993
INVENTOR(S) : T. Michael Dennehey and Joseph C. West, Jr.

It is certified that error appears in the above-identified patent and that said Letters Patent is hereby corrected as shown below:

In claim 10, at column 11, change line 9 to:  -- $R_5 > R_3 > R_2 > R_1$. --

In claim 11, at column 11, change line 10 to:  -- $R_5 > R_4 > R_3 > R_2 > R_1$. --

Signed and Sealed this

Twenty-sixth Day of April, 1994

Attest:

BRUCE LEHMAN

*Attesting Officer*     *Commissioner of Patents and Trademarks*